(12) United States Patent
Maldonado et al.

(10) Patent No.: US 9,669,016 B2
(45) Date of Patent: Jun. 6, 2017

(54) ANTIPARASITIC EFFECT OF BIS[3,5-BIS(BENZYLIDENE)-4-OXO-1-PIPERIDINYL]AMIDE DERIVATIVES

(71) Applicants: THE BOARD OF REGENTS OF THE UNIVERSITY OF TEXAS SYSTEM, Austin, TX (US); UNIVERSITY OF SASKATCHEWAN, Saskatoon (CA)

(72) Inventors: Rosa A. Maldonado, El Paso, TX (US); Miguel A. Vasquez, El Paso, TX (US); Jonathan R. Dimmock, Saskatoon (CA); Umashankar Das, Saskatoon (CA)

(73) Assignees: THE BOARD OF REGENTS OF THE UNIVERSITY OF TEXAS SYSTEM, Austin, TX (US); UNIVERSITY OF SASKATCHEWAN, Saskatchewan (CA)

( * ) Notice: Subject to any disclaimer, the term of this patent is extended or adjusted under 35 U.S.C. 154(b) by 0 days.

(21) Appl. No.: 15/193,589

(22) Filed: Jun. 27, 2016

(65) Prior Publication Data

US 2016/0303105 A1    Oct. 20, 2016

Related U.S. Application Data

(62) Division of application No. 14/684,300, filed on Apr. 10, 2015.

(60) Provisional application No. 61/978,346, filed on Apr. 11, 2014.

(51) Int. Cl.
*A61K 31/13* (2006.01)
*A61K 31/4545* (2006.01)
*A61K 45/06* (2006.01)
*A61K 31/132* (2006.01)

(52) U.S. Cl.
CPC .......... *A61K 31/4545* (2013.01); *A61K 31/13* (2013.01); *A61K 31/132* (2013.01); *A61K 45/06* (2013.01)

(58) Field of Classification Search
CPC ...................... A61K 2300/00; G01N 33/5011
See application file for complete search history.

(56) References Cited

U.S. PATENT DOCUMENTS

| | | | |
|---|---|---|---|
| 5,965,143 A | 10/1999 | Fasel et al. | 424/269.1 |
| 7,566,465 B2 | 7/2009 | Kubata et al. | 424/740 |
| 7,947,741 B2 | 5/2011 | Bostian et al. | 514/637 |
| 2012/0190847 A1 | 7/2012 | Arbiser | 540/592 |

OTHER PUBLICATIONS

Engel et al., (J.Exp. Med. 1998. vol. 188. No. 4:725-734).*
Steverding et al., (Expert Opin. Investig. Drugs 2005. vol. 14.No. 8: 939-955).*

(Continued)

*Primary Examiner* — Ja'Na Hines
(74) *Attorney, Agent, or Firm* — Norton Rose Fulbright US LLP

(57) ABSTRACT

Embodiments are directed to compositions and methods for treating parasitic infections. Compounds have been identified from a library of anti-cancer drugs that serve as suitable agents for targeting trypanosomatids.

7 Claims, 8 Drawing Sheets

(56) References Cited

OTHER PUBLICATIONS

Berman, "Human leishmaniasis: clinical, diagnostic, and chemotherapeutic developments in the last 10 years", *Clinical Infectious Diseases.* 24(4):684-703, 1997.

Berman, "Chemotherapy of leishmaniasis: recent advances in the treatment of visceral disease", *Current Opinion in Infectious Diseases.* 11(6): 707-710, 1998.

International Search Report and Written Opinion issued in PCT/US2015/025482, dated Oct. 8, 2015.

Vasquez, M. "Identification of chemotherapeutic agents against leishmaniasis and Chagas' disease," Thesis, ETD Collection for University of Texas El Paso, Jan. 1, 2013, pp. 1-72 (PDF pp. 1-83). Retrieved from the internet: http://digitalcommons.utep.edu/dissertations/AA13597262 on Sep. 14, 2015.

Vasquez et al. "Evaluation of α, β-Unsaturated Ketones as Antileishmanial Agents", *Antimicrobial Agents and Chemotherapy,* 59(6): 3598-3601, 2015.

\* cited by examiner

A

B

C

Trypanothione (T(SH)₂)    D    Dihydrolipoamide

ANTIPARASITIC EFFECT OF BIS[3,5-BIS(BENZYLIDENE)-4-OXO-1-PIPERIDINYL]AMIDE DERIVATIVES

The present application is a divisional from U.S. application Ser. No. 14/684,300 filed Apr. 10, 2015, which claims priority to U.S. Provisional Application No. 61/978,346 filed Apr. 11, 2014, which are incorporated herein by reference in their entirety.

STATEMENT REGARDING FEDERALLY FUNDED RESEARCH

This invention was made with government support under 2S06GM00812-37 awarded by the National Institutes of Health. The government has certain rights in the invention.

BACKGROUND

Parasitic diseases affect millions of people worldwide with severe social and economic consequences. The protozoan parasites Leishmania major, and Trypanosoma cruzi, cause leishmaniasis and Chagas' disease (CD) respectively. There are several clinical forms of leishmaniasis: visceral leishmaniasis (VL), muco-cutaneous leishmaniasis (MCL), diffuse cutaneous leishmaniasis (DCL) and cutaneous leishmaniasis (CL). As for CD, 15-30% of the people infected with T. cruzi develop manifestations of organ damage, resulting in the cardiac, digestive or nervous forms of chronic Chagas' disease. Currently, there are between 11-18 million individuals infected with T. cruzi, while the overall prevalence of leishmaniasis is 12 million people, with 350 million at risk.

Humans and a wide range of other mammals are usually infected with T. cruzi when the triatomine vector defecates while taking a blood meal. The metacyclic trypomastigote form of the parasite contained in the fecal material is inoculated through the bite wound or mucous membranes. The parasite next invades host cells where it is transformed into intracellular amastigotes. In this stage they proliferate by binary fission and eventually differentiate into trypomastigotes. The host cell finally ruptures releasing the parasites into the circulation where they can invade other cells or be ingested in a blood meal by the insect vector. Leishmania on the other hand, is transmitted by sand flies as metacyclic promastigotes. The proliferative promastigote form then differentiates into the metacyclic form before entering the mammalian host. Once inside the host, the metacyclic form is phagocytosed by macrophages where they differentiate into amastigotes, which proliferate leading to macrophage lysis and further infection of surrounding macrophages.

Despite the advances in understanding the biology of these organisms, most of the drugs still used were developed in colonial times. The current treatment for T. cruzi consists of two nitroheterocyclic derivatives, benzinidazol and nifurtimox. These compounds have severe side effects and since the course of treatment lasts from 1-4 months resulting in many incomplete drug schedules, which leads to the development of resistance. In the case of leishmaniasis, pentavalent antimonials are used throughout most endemic regions; however, they are no longer used in India because of drug resistance. In the 1980s, new formulations of amphotericin B encapsulated in liposomes were developed. This drug is highly effective in both VL and CL; however, its high cost limits the wider use of this drug. Despite the ever-increasing need for safe and effective new drugs, their development has been extremely slow.

Thus there is a need for additional drugs against and treatments for Leishmania major or Leishmania species and T. cruzi.

SUMMARY

Certain embodiments are directed to methods of treating eukaryotic parasites comprising administering an effective amount of an α,β-unsaturated ketone or bis[3,5-bis(benzylidene)-4-oxo-1-piperidinyl]amide derivative. In certain aspects the α,β-unsaturated ketone or bis[3,5-bis(benzylidene)-4-oxo-1-piperidinyl]amide derivative is NC2459, NC901, or NC884. In certain aspects the α,β-unsaturated ketone or bis[3,5-bis(benzylidene)-4-oxo-1-piperidinyl]amide derivative is administered at a dose of between 50, 100, 150, 200, 250, 300, 400 500 to 250, 300, 350, 400, 450, 500, 550, 600, 700, 800, 900 mg/day, including all values and ranges there between. In certain aspects 50, 100, 150, 200, 250, 300, 350, 400, 450, 500, 550, 600, 700, 800, 900, 1000 mg of α,β-unsaturated ketone or bis[3,5-bis(benzylidene)-4-oxo-1-piperidinyl]amide derivative is administered. In a further aspect the α,β-unsaturated ketone or dose of bis[3,5-bis(benzylidene)-4-oxo-1-piperidinyl]amide derivative is administered in one dose or in multiple doses over 0.5, 1, 2, 3, 4, 5, 6, 7, 8, 9, or 10 minutes, hours or days. The α,β-unsaturated ketone or bis[3,5-bis(benzylidene)-4-oxo-1-piperidinyl]amide derivative can be formulated as a tablet, a capsule, or a solution. In certain aspects the α,β-unsaturated ketone or bis[3,5-bis(benzylidene)-4-oxo-1-piperidinyl]amide derivative is administered orally or intravascularly. In certain aspects the α,β-unsaturated ketone or bis[3,5-bis(benzylidene)-4-oxo-1-piperidinyl]amide derivative can be administered in combination with other antiparasite therapies. In certain embodiments the parasite is Leishmania major or Trypanosoma cruzi. In certain aspects the bis[3,5-bis(benzylidene)-4-oxo-1-piperidinyl]amide derivative is NC2459 and the α,β-unsaturated ketone is NC901 or NC884

Formula I

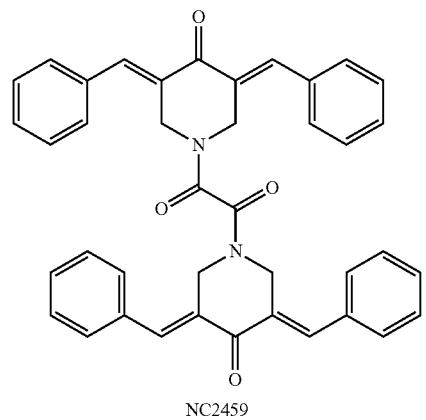

NC2459

Formula II

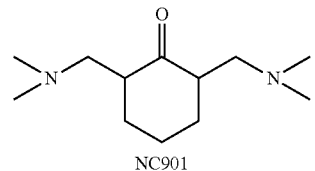

NC901

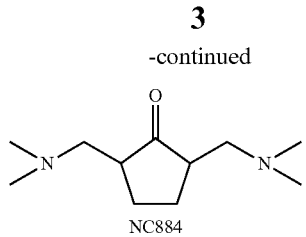

Formula III

NC884

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

Figure 1A:
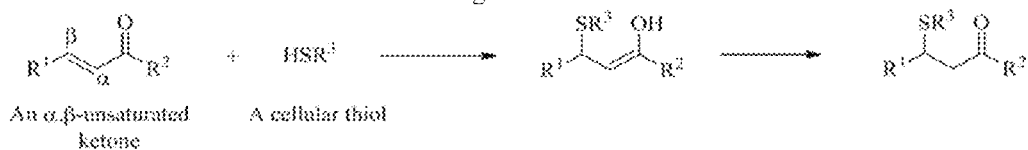
FIG. 1A-1D. (A) The reaction of α,β-unsaturated ketones with thiols. (B) Structures of NC901 and NC884 as well as the perceived manner in which reaction with thiols takes place. (C) Structure of NC2459 indicating the potential sites where interactions with thiols can occur. (D) Structures of two essential thiol molecules found in trypanosomatids, trypanothione (reduced form) and dihydrolipoamide.
Figure 1B:
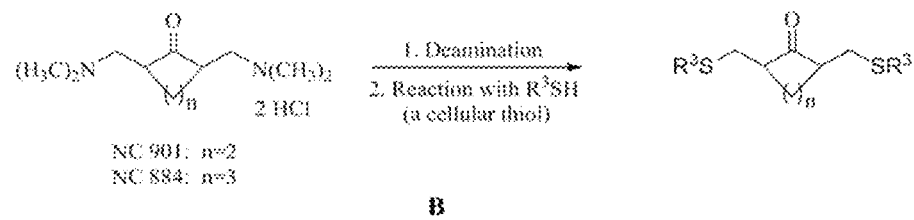
Figure 1C:
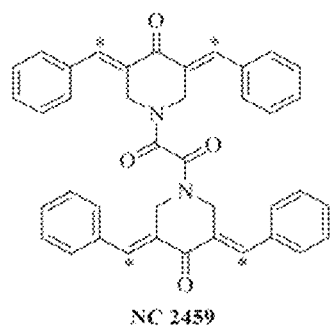
Figure 1D:
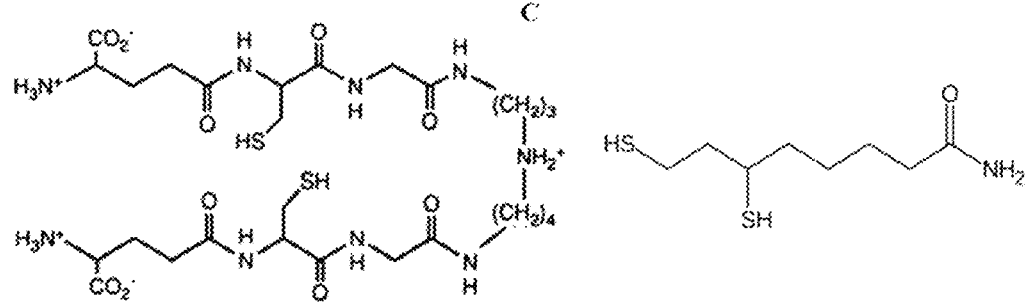

Trypanosomatids are a group of kinetoplastid protozoa distinguished by having only a single flagellum. All members are exclusively parasitic, found primarily in insects. A few genera have life-cycles involving a secondary host, which may be a vertebrate, invertebrate or plant. These include several species that cause major diseases in humans. The three major human diseases caused by trypanosomatids are—African trypanosomiasis (Sleeping Sickness, caused by *Trypanosoma brucei* and transmitted by Tsetse flies), South American trypanosomiasis (Chagas Disease, caused by *Trypanosoma cruzi* and transmitted by triatomine bugs), and leishmaniasis (a set of trypanosomal diseases caused by various species of *Leishmania* transmitted by sandflies). Certain aspects described herein are directed to compounds and therapies for treating trypanosomatid infections.

Therapies against human leishmaniasis include pentavalent antimonials (sodium stibogluconate and meglumine antimonate) and amphotericin B (Berman, *Clinical Infectious Diseases*. 24(4):684-703, 1997; Berman, *Current Opinion in Infectious Diseases*. 11(6): 707-710, 1998). Paromomycin, an aminoglycoside, has also shown anti-*Leishmania* activity, but few patients have been treated and the efficacy has been variable in different areas of the world where it was studied (Berman, *Current Opinion in Infectious Diseases*. 11(6):707-710, 1998). These drugs have several disadvantages: (1) their cost is prohibitively high; (2) they are unavailable for oral administration (some of them like amphotericin B can only be used intravenously); and/or (3) they may cause serious side effects that require close monitoring of the patients (Berman, *Clinical Infectious Diseases*. 24(4):684-703, 1997).

In order to identify additional compounds for the treatment of parasitic infections a library of compounds was screened to identify compounds having anti-parasitic properties using *Leishmania major* and *Trypanosoma cruzi* as model target organisms. The molecules analyzed contain at least one α,β-unsaturated ketone group or are capable of generating this functionality when administered to a subject (FIG. 1). α,β-unsaturated ketones (referred to as enones) react preferentially or exclusively with cellular thiols in contrast to amino or hydroxy functionalities present in protein and DNA. The absence of enone interaction with nucleic acids leads to less adverse genotoxic effects. These compounds were prepared initially as candidate cytotoxins and a number of them have $IC_{50}$ values in the submicromolar and low micromolar range. Trypanosomatids are known to contain novel thiols that have been validated as drug targets, such targets include trypanothione and dihydrolipoamide (FIG. 1). Trypanothione is involved in many essential pathways that are unique to trypanosomatids and is also known to be more reactive than known enone targets, e.g., glutathione (GSH).

In certain embodiments an antineoplastic drug library is evaluated utilizing luciferase expressing *L. major* parasites to identify compounds active against *L. major*. The most active compounds identified from the drug screening analysis on *L. major* promastigotes were also effective at inhibiting the amastigote form of *L. major* as well as the insect and human forms of *T. cruzi*. To confirm the importance of these results, the compounds were analyzed for their activity in vivo on a mouse model for cutaneous leishmaniasis. The compounds were determined to act through an apoptosis-like mechanism that is induced by the dissipation of the mitochondrial membrane potential ($\Delta_{\psi m}$) resulting in the death of *L. major*.

Figure 2:
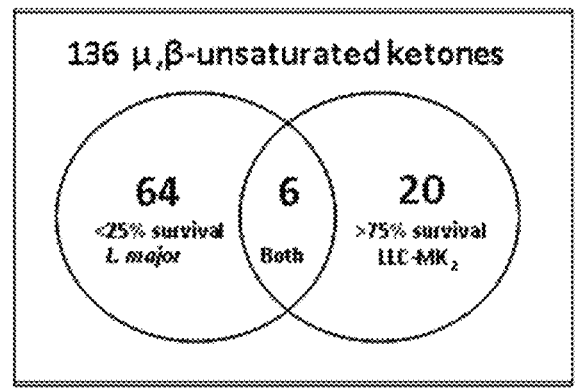
FIG. 2. Drug screening results and criteria for identifying potential drug candidates. The NC library (Dimmock's library) of 136 compounds was screened for anti-parasitic and cytotoxic activity to mammalian cells (LLC-MK$_2$). The criteria used to identify potential hits were the observance of less than 25% survival of L. major promastigotes and greater than 75% survival in LLC-MK$_2$ cells. Six compounds met these criteria and additional toxicity assays narrowed down the number of candidate compounds to three.
Figure 3:
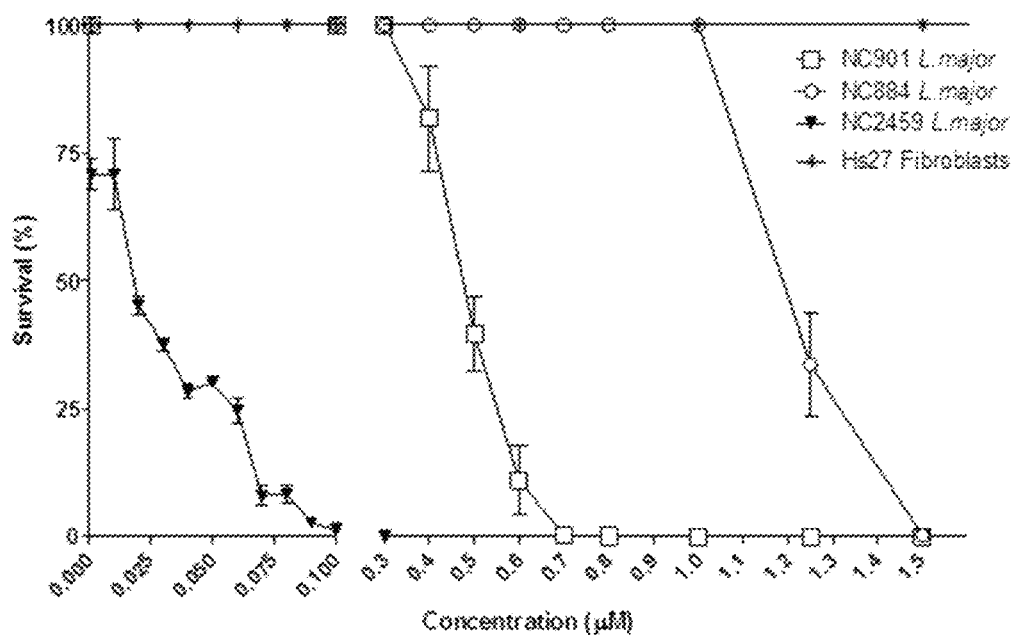
FIG. 3. Evaluation of the leishmanicidal activity of NC884, NC901, and NC 2459. The survival of the parasites and human fibroblast was determined after a 96 hour incubation period. All three compounds exhibited a much higher degree of toxicity to the parasites than to the human cell line. The EC$_{50}$ was determined for each of these cell lines and is displayed in Table 1 (p-value<0.0001).
Figure 4:
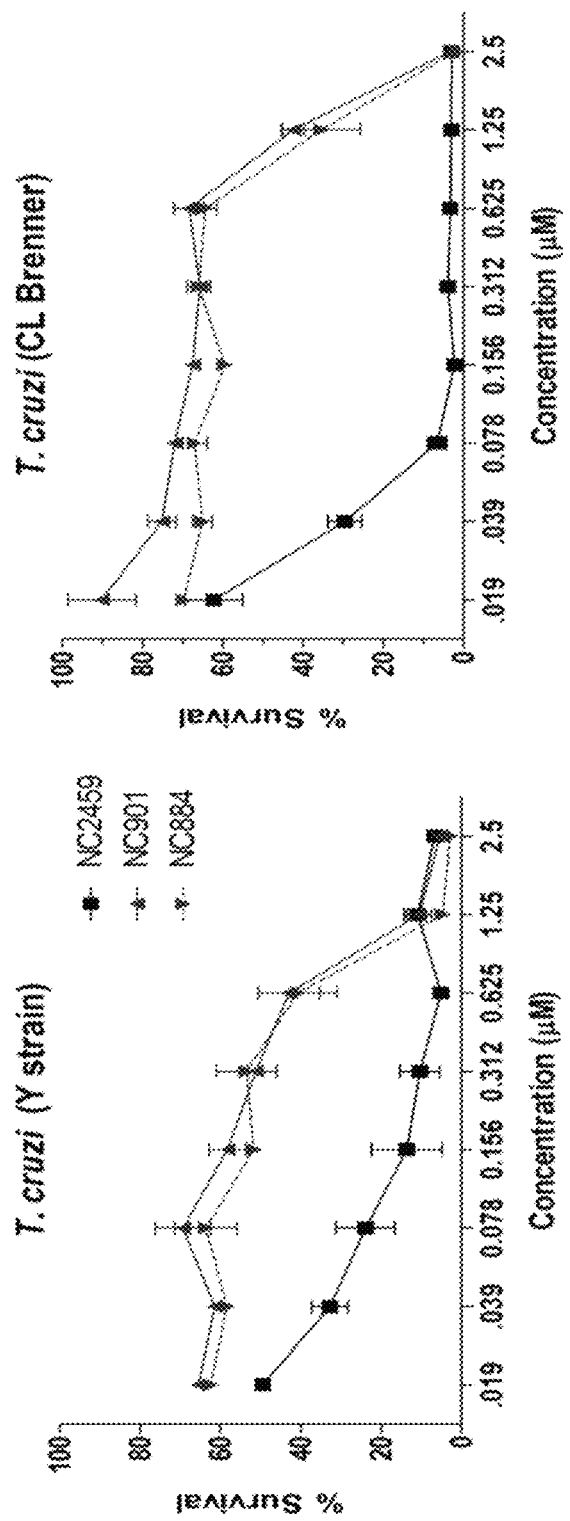
FIG. 4. Evaluation of compounds NC2459, NC901, and NC884 in T. cruzi epimastigotes. The survival percentage of T. cruzi epimastigotes (Y strain and CL Brenner) was determined at various concentrations compound. All three compounds exhibited an EC$_{50}$ at nanomolar concentrations as displayed in Table 1 (p-value<0.0001).

In certain embodiments α,β-unsaturated ketone derivatives (NC series), initially developed as anti-cancer drugs, were evaluated against *L. major* promastigotes, *T. cruzi* epimastigotes, and four types of mammalian cells. The majority of the 136 compounds screened using high throughput screening (HTS) assays displayed a high degree of cytotoxicity towards *L. major* promastigotes with a low degree of toxicity towards the LLC-$MK_2$ cells (FIG. 2). Upon evaluation of the difference in toxicities between the parasites and different mammalian cell types, three (NC901, NC884, and NC2459) of the 136 compounds in the drug library showed potent anti-parasitic activity with no cytotoxicity to mammalian cells at low nanomolar-micromolar concentrations (FIG. 3). Analysis of these three compounds on the insect form of *T. cruzi* resulted in similar $EC_{50}$ values observed in *L. major* promastigotes (FIG. 4). The most potent compound, NC2459, had a minimum of a 100-fold difference in toxicity between both parasites and all mammalian cell types tested.

Figures 5A, 5B, 5C:
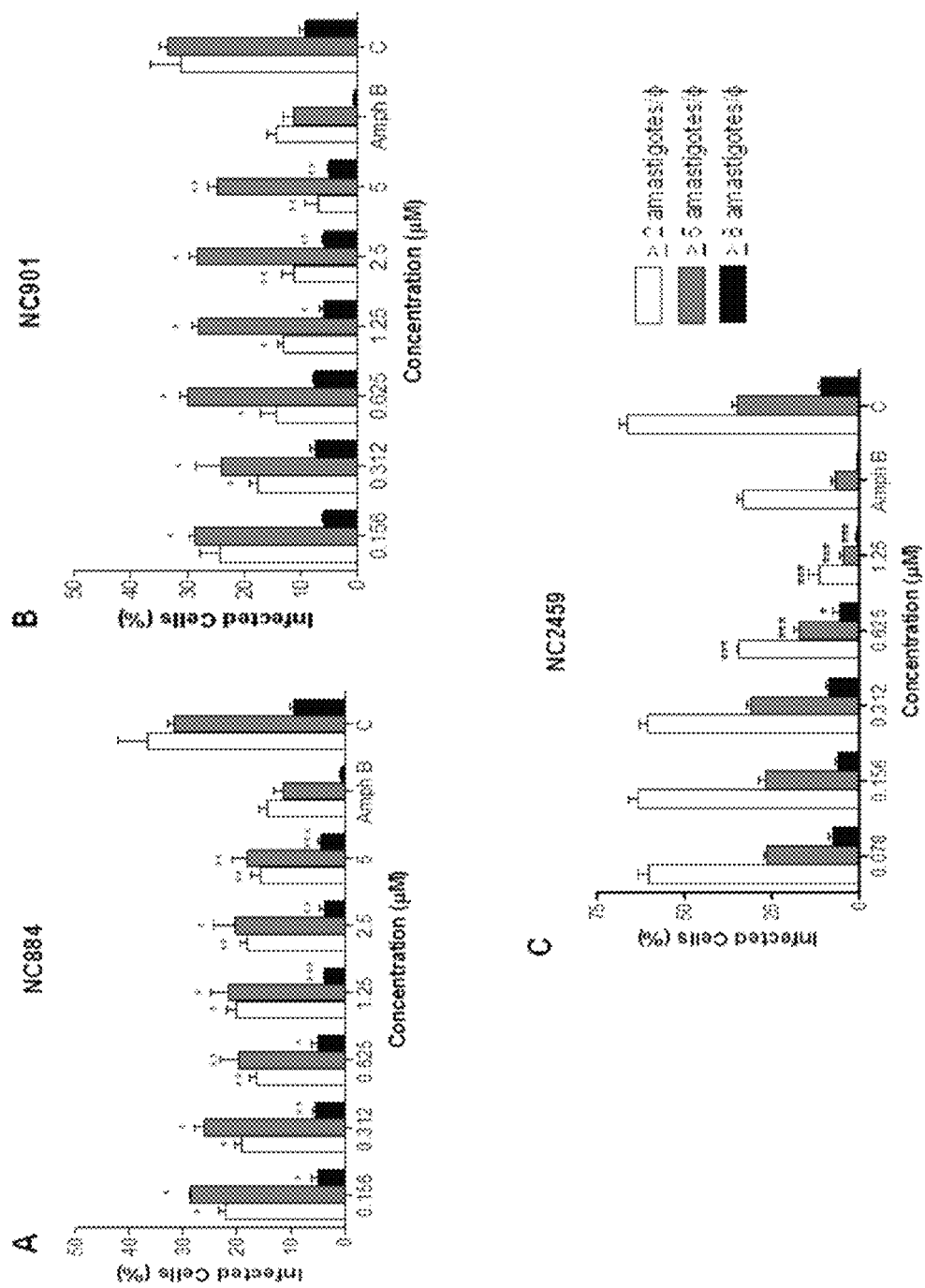
FIG. 5A-5C. Antiproliferative activity of NC884, NC901, NC2459 on L. major amastigote-infected macrophages in vitro. Peritoneal murine macrophages were isolated from BALB/c mice and infected with L. major metacyclic promastigotes. 48 hours after infecting with parasites, compounds were added and incubated for 48 hours before being fixed with 4% paraformaldehyde and stained with DRAQ5®. Infected cells were analyzed using the BD Pathway™ Bioimager and screened for constraints of 2, 5, and 8 or more amastigotes per cell. (A) Compound NC884 given at concentrations ranging from 0.156-5 μM. (B) Compound NC901 given at concentrations ranging from 0.156-5 (C) Compound NC2459 given at concentrations ranging from 0.078-1.25 μM. p≤0.05(*), p≤0.01(), and p≤0.001(*). Amph B, Treated with 5 μM amphotericin B; C, 1% DMSO. The Z-factors calculated for the assays are in the range of 0.5 to 0.91, indicating that the quality of the assay is excellent.
Figure 6:
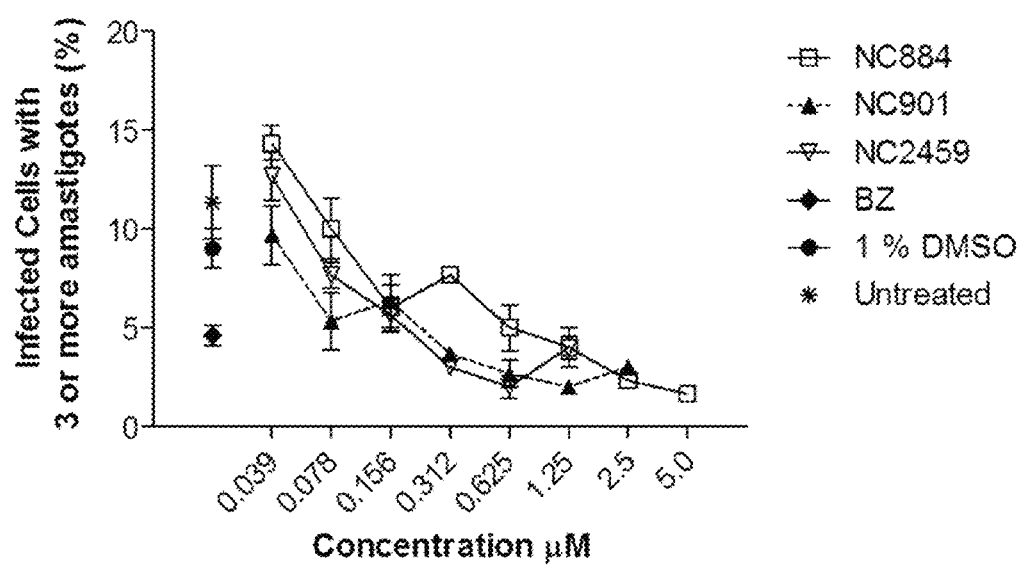
FIG. 6. Antiproliferative activity of NC884, NC901, NC2459 on T. cruzi amastigote-infected human osteoblasts in vitro. Human osteoblasts were plated and infected with T. cruzi trypomastigotes. After infecting with parasites compounds were added and incubated for 48 hours before being fixed with 4% paraformaldehyde and stained with DRAQ5®. Infected cells were analyzed using the BD Pathway™ Bioimager and screened for constraint of 3 or more amastigotes per cell. p≤0.05(*), p≤0.01(), and p≤0.001(*). BZ, 800 μM benznidazole (positive control); 1% DMSO, diluent control. The Z-factor is 0.5 indicates that the quality of the assay is good.

NC901, NC884, and NC2459 were tested against the intracellular forms of *L. major* and *T. cruzi* using infectivity assays. These studies determine the potential activity of a given compound in vivo since the parasites are being treated while replicating within their natural host cells. All three compounds (NC901, NC884, and NC2459) significantly reduced the parasite burden in *L. major* and *T. cruzi* infected mammalian cells (FIG. 5 and FIG. 6, respectively).

Figures 7A, 7B, 7C, 7D:
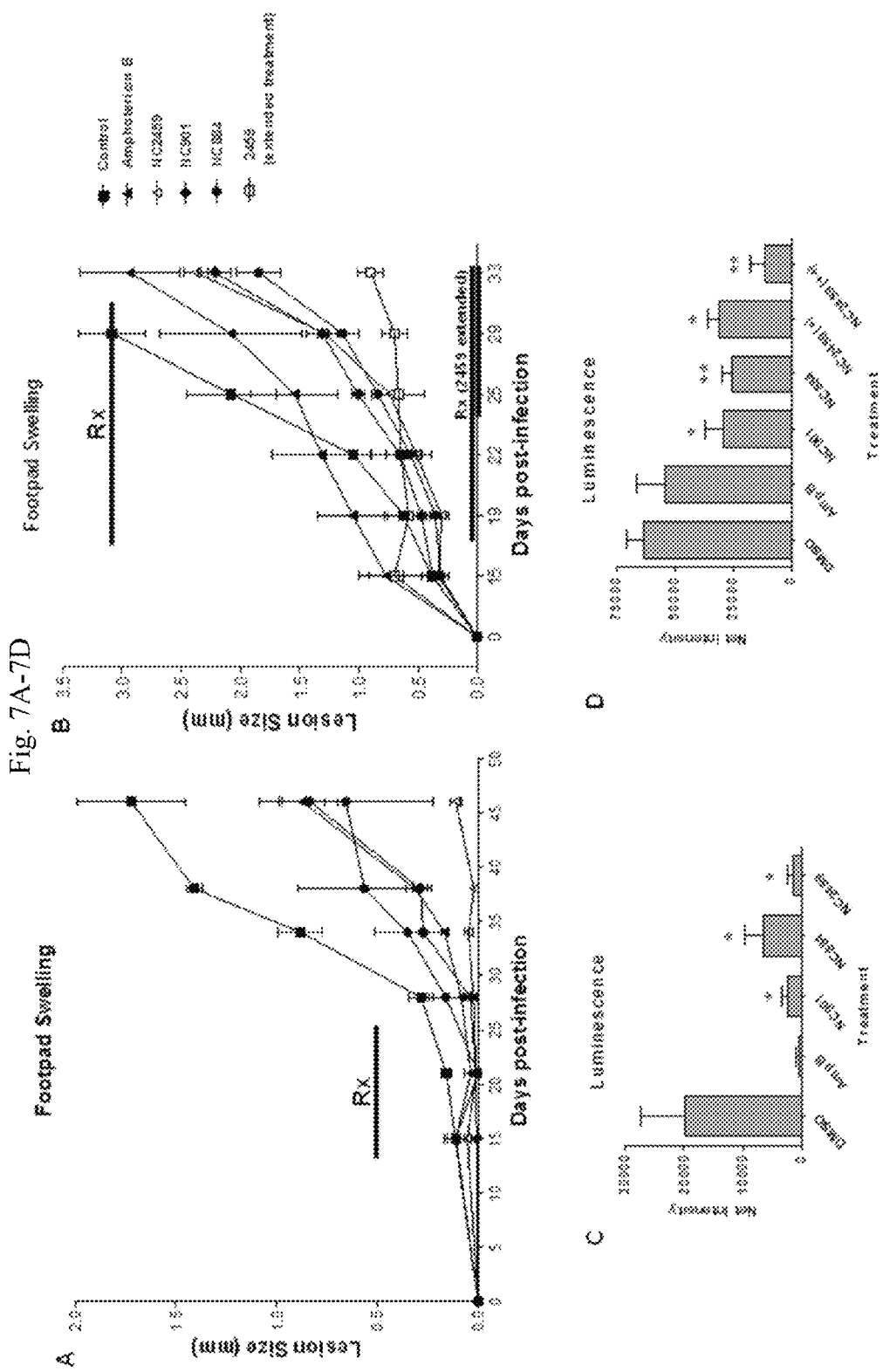
FIG. 7A-7D. In vivo activity of compounds NC901, NC884, and NC2459 in BALB/c mice infected with L. major. (A and B) Footpad size of BALB/c mice infected with $10^5$ and $10^6$ L. major metacyclic promastigotes respectively. All three compounds caused a decrease in lesion size compared to the DMSO control at 46 days post-infection. Rx line refers to the time period in which treatment was administered daily. Double Rx line indicates that the daily dosage of NC2459 was doubled for that time period. (C and D) Luminescence of BALB/c mice footpad at 46 days post infection with $10^5$ and $10^6$ L. major metacyclic promastigotes respectively. Luminescence for each mouse infected footpad was determined at 33 days p.i. Each compound resulted in a significant decrease in lesion size in comparison to the DMSO control at 29 days p.i. (p≤0.05) Statistical analysis was carried out using the two-sided unpaired t-test.

The compounds were tested in an in vivo model for cutaneous leishmaniasis. These compounds reduced the physical burden caused by these parasites within a localized area without any obvious toxic side effects when treated through the intraperitoneal route. In FIG. 7A, compounds NC901 and NC884 reduced the footpad swelling similar to that of the positive control (Amphotericin B), while compound NC2459 clearly exhibited a much lower amount of swelling than all groups. In the second treatment (FIG. 7B), the dosages were increased and all experimental groups showed significantly smaller lesion sizes than that of the control group at four weeks post-infection, while compound NC2459 given at 8 mg/kg/day was much more effective than all treated groups at 33 days post-infection. There were also no signs of toxicity in all experimentally treated groups in the hyper-infection experiment.

In certain embodiments the compounds are formulated for administration to subject having a parasite infection, located in a geographic region endemic to a parasite, or are at risk of parasite infection, e.g., are present in a local area in the midst of an outbreak. Acceptable formulation components for pharmaceutical preparations are nontoxic to recipients at the dosages and concentrations employed. In addition to the anti-parasitic agents that are provided, compositions may contain components for modifying, maintaining, or preserving, for example, the pH, osmolarity, viscosity, clarity, color, isotonicity, odor, sterility, stability, rate of dissolution or release, adsorption, or penetration of the composition. Suitable materials for formulating pharmaceutical compositions include, but are not limited to, amino acids (such as glycine, glutamine, asparagine, arginine or lysine); antimicrobials; antioxidants (such as ascorbic acid, sodium sulfite or sodium hydrogen-sulfite); buffers (such as acetate, borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophobic polymers (such as polyvinylpyrrolidone); low molecular weight polypeptides; salt-forming counter ions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (see Remington's Pharmaceutical Sciences, 18 th Ed., (A. R. Gennaro, ed.), 1990, Mack Publishing Company), hereby incorporated by reference.

Formulation components are present in concentrations that are acceptable to the site of administration. Buffers are advantageously used to maintain the composition at physiological pH or at a slightly lower pH, typically within a pH range of from about 4.0 to about 8.5, or alternatively, between about 5.0 to 8.0. Pharmaceutical compositions can comprise TRIS buffer of about pH 6.5-8.5, or acetate buffer of about pH 4.0-5.5, which may further include sorbitol or a suitable substitute therefor.

The pharmaceutical composition to be used for in vivo administration is typically sterile. Sterilization may be accomplished by filtration through sterile filtration membranes. If the composition is lyophilized, sterilization may be conducted either prior to or following lyophilization and reconstitution. The composition for parenteral administration may be stored in lyophilized form or in a solution. In certain embodiments, parenteral compositions are placed into a container having a sterile access port, for example, an intravenous solution bag or vial having a stopper pierceable by a hypodermic injection needle, or a sterile pre-filled syringe ready to use for injection.

The above compositions can be administered using conventional modes of delivery including, but not limited to intravenous, intraperitoneal, oral, or intraarterial. In certain aspects an anti-parasitic agent will be administered orally. When administering the compositions by injection, the administration may be by continuous infusion or by single or multiple boluses. For parenteral administration, the anti-parasitic agents may be administered in a pyrogen-free, parenterally acceptable solution comprising the desired anti-parasitic agents in a pharmaceutically acceptable vehicle. A particularly suitable vehicle for parenteral injection is one in which one or more anti-parasitic agents are formulated as a sterile solution and properly preserved.

Once the pharmaceutical composition of the invention has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

If desired, stabilizers that are conventionally employed in pharmaceutical compositions, such as DMSO, oil, sucrose, trehalose, or glycine, may be used. Typically, such stabilizers will be added in minor amounts ranging from, for example, about 0.1% to about 0.5% (w/v). Surfactant stabilizers, such as TWEEN®-20 or TWEEN®-80 (ICI Americas, Inc., Bridgewater, N.J., USA), may also be added in conventional amounts. In certain aspects the composition are 10 to 30% DMSO and/or oil (e.g., sesame oil).

The components used to formulate the pharmaceutical compositions are preferably of high purity and are substantially free of potentially harmful contaminants (e.g., at least National Food (NF) grade, generally at least analytical grade, and more typically at least pharmaceutical grade). Compositions for parental administration are also sterile, substantially isotonic and made under GMP conditions.

For the compounds of the present invention, alone or as part of a pharmaceutical composition, such doses are between about 0.001 mg/kg and 1 mg/kg body weight, preferably between about 1 and 100 µg/kg body weight, most preferably between 1 and 10 µg/kg body weight.

Therapeutically effective doses will be easily determined by one of skill in the art and will depend on the severity and course of the disease, the patient's health and response to treatment, the patient's age, weight, height, sex, previous medical history and the judgment of the treating physician.

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example I

In Vitro Evaluation of Antiparasitic and Cytotoxic Effects

It has been Previously Reported that Various Enones or Thiol Alkylators Induce apoptosis in pancreatic cancer cells through the depletion of mitochondrial glutathione (GSH). Therefore, to further understand the mechanism of action in the parasite it was determined that compounds NC901, NC884, and NC2459 induce annexin V binding in *L. major* promastigotes at concentrations that do not affect intraperitoneal macrophages. Moreover, the results suggest that the induction of this apoptosis-like effect in *L. major* promastigotes is mitochondrial dependent as treatment of these parasites with all three compounds resulted in the depolarization of the mitochondrial membrane potential ($\Delta_{\psi m}$).

Based on the characteristics of the NC library, these compounds may be interfering with the essential trypanosomatid unique pathway known as thiol or trypanothione metabolism. Some of these previously established characteristics include the ability for these compounds to target cellular thiols and lower cellular levels of glutathione as well as inhibit the isoenzyme of glutathione S-transferase in human pancreatic cell lines. Additionally, these compounds are known to be cytotoxic thiol alkylators, meaning that they have the capability to spontaneously react with thiol groups present in low molecular weight molecules.

Preliminary data has shown that compounds NC901 and NC884 are irreversible inhibitors of the primary enzyme involved in the trypanothione pathway, trypanothione reductase (TR) from *T. cruzi*, as well as a structurally and functionally similar enzyme, known as lipoamide dehydrogenase (LipDH) also from *T. cruzi*. These two enzymes both play many critical roles within all stages of the parasites' life cycle including the responsibility of eliminating toxic ROS that is constantly encountered by the parasite as well as many other essential functions. Both compounds NC901 and NC884 exhibited a time-dependent irreversible inhibition of both enzymes with LipDH exhibiting a more significant level of inhibition than TR (unpublished data). Interestingly, the compound that was more cytotoxic towards the parasites (NC901) was also the more potent inhibitor of these two enzymes.

It has been suggested that LipDH activates thiol containing molecules, such as trypanothione and tryparedoxins, within the mitochondrion of *T. cruzi*. Inhibition of LipDH within the mitochondrion of *L. major* and *T. cruzi* may be causing adverse effects in the parasites by compromising the integrity of the mitochondrial membrane. Trypanothione and dihydrolipoamide require two thiol groups in order to be in their active forms. It has been established that these molecules carry out many essential functions within both *L. major* and *T. cruzi* parasites. The fact that these compounds have very similar effects and $EC_{50}$ values against different species of parasite may indicate that they are acting on the substrates which are structurally identical in these parasites. It is plausible that these compounds may be inhibiting TR and LipDH as well as their substrates resulting in a compounded negative effect against the parasites. This is known to be the case for the compound melarsenoxide, which is currently used to combat *Trypanosoma brucei*, the causative agent of African sleeping sickness. Melarsenoxide inhibits TR and LipDH while forming stable 1:1 complexes with dithiols trypanothione (T(SH)$_2$) and dihydrolipoamide. This would explain why these compounds are far more toxic to the parasites than they are to the mammalian cells.

A. Results

In these experiments, the novel NC chemical library of 136 compounds was screened for anti-parasitic and cytotoxic activity to mammalian cells. Compounds were incubated with *Leishmania major* promastigotes or LLC-MK$_2$ cells for 96 hours and were analyzed for toxicity. As summarized in FIG. 2, 64 of these compounds effectively inhibited the survival of *L. major* promastigotes by 75% or greater. At the same concentrations 20 compounds displayed minimal to no toxicity (>75% survival) when treated against LLC-MK$_2$ cells. Out of the 64 and 20 compounds that met the initial criteria, six of these compounds met the criteria for both anti-parasitic activity and cytotoxicity to mammalian cells. These six compounds were then tested in several mammalian cell lines. The mammalian cells screened for toxicity were Hs27 human fibroblasts, LLC-MK$_2$ cells, RAW 264.7 murine macrophages, and BALB/c intraperitoneal macrophages. *L. major* promastigotes were also tested at various concentrations to determine the $EC_{50}$ after 24, 48, 72, and 96 hour treatment periods. After a 96 hour treatment, the estimated $EC_{50}$ calculated using t-test and linear regression analysis for compounds NC901, NC884, and NC2459 were 453 nM, 1.12 µM, and 20 nM, respectively (FIG. 3).

After evaluating the six compounds in several mammalian cell lines, only three compounds (NC901, NC884 and NC2459) showed a significant difference between the concentrations needed for anti-parasitic activity and cytotoxicity to mammalian cells. All three of these compounds exhibited a 10-fold or greater difference between the $EC_{50}$ of the parasites and the $IC_{50}$ of all three mammalian cell lines with the exception of a 7-fold difference for compound NC884 when treated against murine macrophages (Table 1). Compound NC2459 showed a minimum of a 100-fold difference between the $EC_{50}$ for the parasites and for all three mammalian cell lines.

TABLE 1

Summary of $IC_{50}$ and $EC_{50}$ for each compound (NC901, NC884, and NC2459) tested against parasites and mammalian cells.

| | Mammalian cells $IC_{50}$ (µM) ± SD | | | *L. major* | | *T. cruzi* | |
|---|---|---|---|---|---|---|---|
| Compounds | Peritoneal Murine Macrophages | LLC-MK$_2$ | Hs27 Fibroblasts | Promastigotes $EC_{50}$ (µM) [TI] | Intracellular Amastigotes $IC_{50}$ (µM) | Epimastigotes $EC_{50}$ (µM) [TI] | Intracellular Amastigotes $IC_{50}$ (µM) |
| NC901 | 7.03 ± 0.42 | 8.02 ± 0.25 | 16.0 ± 0.12 | 0.45 [35] | 1.87 ± 0.20 | 0.468 [34.19] | 0.301 ± 0.09 |
| NC884 | 7.67 ± 0.31 | 15.1 ± 0.33 | 16.3 ± 0.17 | 1.12 [14.2] | 0.937 ± 0.13 | 0.475 [33.7] | 0.987 ± 0.11 |
| NC2459 | 5.45 ± 0.36 | 2.0 ± 0.093 | 10.01 ± 0.09 | 0.020 [500] | 0.625 ± 0.11 | 0.020 [500] | 0.227 ± 0.04 |

$EC_{50}$: Half maximal effective concentration calculated with 95% confidence interval;
± values are the estimated $EC_{50}$ interval.
TI: Therapeutic Index ($IC_{50}$ in Hs27 human fibroblasts)/($EC_{50}$ in parasites).
p-value < 0.0001 for all concentrations.

To determine whether these compounds (NC901, NC884, and NC2459) are active against *T. cruzi*, the compounds were tested with non-infective epimastigote forms of *T. cruzi* from the CL Brenner and Y strains. After a 96 hour incubation period, all three compounds effectively inhibited the viability of the CL Brenner and Y strain of *T. cruzi* epimastigotes (FIG. 4). The respective $EC_{50}$ concentrations were 468 nM, 475 nM, and 20 nM. Therefore, not only do these compounds display toxicity towards *T. cruzi* epimastigotes, they also exhibit very similar $EC_{50}$ concentrations required for inhibiting *T. cruzi* (Y strain) epimastigote's survival as in *L. major* promastigotes in vitro (Table 1). It was observed that compound NC884 had a greater than 2-fold difference in toxicity against *T. cruzi* (Y strain) as in *L. major*.

In summary, these compounds have shown to be significantly more toxic to the parasites in comparison to the mammalian cell lines (Table 1). Compounds NC901, NC884, and NC2459 have shown to have potent anti-trypanosomal effects against the insect form of both *L. major* and *T. cruzi*.

The difference in toxicity observed between the parasites and mammalian cells led to further experiments on intracellular amastigotes; the proliferative form of the parasites that replicate within the human host.

Evaluation of the Anti Proliferative Activity on Intracellular Amastigotes from *L. major* and *T. cruzi* Using High-Content Imaging.

In vitro infectivity experiments were carried out to determine the activity of compounds NC901, NC884, and NC2459 against *L. major* intracellular amastigotes. Intraperitoneal macrophages isolated from BALB/c mice were infected with *L. major* metacyclic promastigotes. After the parasites were allowed to establish infection for 48 hours, the compounds were added and incubated for an additional 48 hours. The compounds anti-leishmanial activity was evaluated using the BD Pathway Bioimager™. In the analysis several constraints were used, such as 2, 5, and 8 or more amastigotes per macrophage. In comparison to the 1% DMSO treated control all three compounds showed a significant decrease in the percentage of infected cells under all three constraints using the unpaired t-test statistical analysis (FIG. 5). The most effective concentration for compounds NC901 and NC884 was 5 μM, while compound NC2459 was most effective at a concentration of 1.25 μM. Compounds NC901 and NC884 were not as effective as the positive control amphotericin B at the same concentration of 5 μM, however, compound NC2459 was significantly more effective at decreasing the percentage of infected macrophages under the constraint of two or more parasites per macrophage.

Human osteoblasts were infected with *T. cruzi* trypomastigotes and were treated with each compound at multiple concentrations for 48 hours. 96 well plates were evaluated using the BD Pathway Bioimager™ and analyzed under the constraint of 3 or more amastigotes per cell (Z-factor=0.41 indicating that is an aceptable assay). All three compounds displayed a significant decrease in the percentage of infected cells (p≤0.05 unpaired t-test statistical analysis) (FIG. 6). The compounds were effective in a concentration range of 156 nM to 5 with the most potent compound being NC2459 exhibiting an $IC_{50}$ of 227 nM. All three compounds were shown to be more effective than the positive control and standard drug benznidazole at 800 μM.

Assessment of the Compounds' Anti-Parasitic Activity on a Murine Model for Cutaneous Leishmaniasis.

Two experiments were performed to explore the efficacy of the three most active compounds against *L. major* infections in BALB/c mice. In the first set of experiments, the mice were infected with $10^5$ *L. major* metacyclic promastigotes (Table 2, FIG. 7A). All three compounds and amphotericin B resulted in reduced footpad swelling compared to the non-treated controls throughout the course of the experiment (FIG. 7A). At 46 days post-infection all experimentally treated groups exhibited a lesion size smaller than or equal to that of the positive control group treated with amphotericin B.

Further evidence of this result was observed by determining the relative amount of luminescence emitted from the luciferase expressing parasites in the infected footpad for each mouse in the study at 46 days post-infection (FIG. 7A). The most effective compound at controlling the swelling of the footpad was compound NC2459. Lesions for all mice in the NC2459 treated group did not start developing measurable lesions until 2 to 3 weeks after the last treatment (total of 6-7 weeks post-infection), furthermore, one out of the three mice never developed a lesion at all after monitoring for up to twelve weeks post-infection. PCR of the *L. major* MetAP1 gene showed no traces of *L. major* genomic DNA in the footpad of the mouse displaying no lesion treated with NC2459 in comparison to the PCR from one of the infected control mice.

To determine the relative toxicity of a compound, weights were analyzed since a reduction in weight is a good indication for toxicity of a drug. There was a slight reduction in weight for all groups in the third week post-infection with a much more dramatic loss in weight for only the amphotericin B treated group. This was expected since amphotericin B is already known to be highly toxic in mammalians. Mice treated with the three compounds (NC901, NC884, and NC2459) continued to lose a slight amount of weight in the 4th week post-infection as did the DMSO treated control. This pattern of weight loss may be attributed to the physical stress (DMSO IP injections and physical manipulation) that these mice endure on a daily basis during treatment. Nevertheless, there was no significant weight loss for any of the groups except for the mice receiving amphotericin B. After treatment was abolished weights for all groups went back to normal. Additionally, no mice died as a result of the compounds toxicity.

In the in vivo experiment shown in FIG. 7B (hyper-infection), mice were infected with $10^6$ *L. major* metacyclic promastigotes rather than $10^5$ in order to determine the activity of these compounds in a more pronounced infection. This experiment consisted of 26 female BALB/c mice organized in four groups of five and one group of six. All experimental groups were given higher doses of compound as summarized in Table 2. After two weeks post-infection, prior to the first treatment, all mice displayed visible and measurable lesions five times larger than in the first trial of experiments. These lesions also grew much more rapidly throughout the course of the infection than beforehand (FIG. 7B). After four weeks post-infection all three NC compounds displayed the ability to significantly reduce the lesion size in *L. major* infected mice in comparison to the control group (p≤0.05). The luminescence detected from the infected footpads for each group concurred with this observation when analyzed at 29 days post-infection. At this time point, the mice in the control group were no longer allowed to continue the experiment to avoid physical distress caused by such a large lesion, however, all other groups were monitored for an additional four days. After one week of treatment with compound NC2459, three of the mice from this group were given double the daily dose of drug (8 mg/kg/day) while the other three remained on the same daily dose (4 mg/kg/day). The three mice given the higher dose were also treated for an extra four days of treatment or four additional daily doses. This group is referred to as, NC2459 extended treatment group (FIG. 7B). Not only did doubling the dose to 8 mg/kg/day decrease the growth rate of the lesion, but at 33 days post-infection this group had a significantly smaller lesion than all other groups (p≤0.05). The increase in dosage for the NC2459 extended treatment group did not result in any additional weight loss or toxic side effects compared to the control group, as was the case for all other treated groups. For all groups, the removal of treatment resulted in an increase in the rate at which the lesion grew, thus the presence of compound was critical to keeping the lesion size at a minimum in this experiment.

α,β-Unsaturated Ketones Derivatives Induce Apoptosis-Like Effect and Mitochondrial Hyperpolarization in *L. major* Promastigotes.

Figures 8A, 8B, 8C:
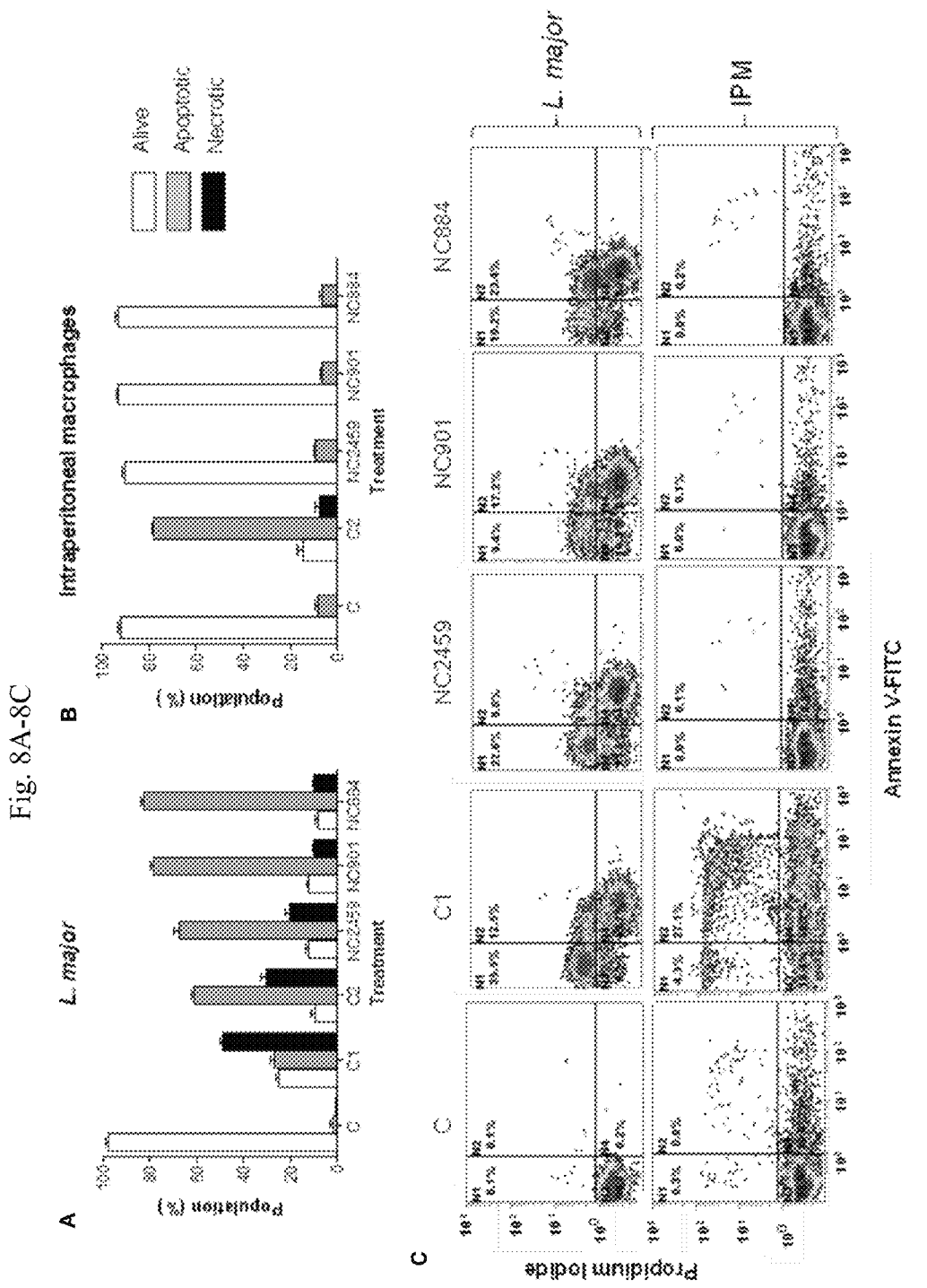
FIG. 8A-8C. The compounds NC901 (2.5 µM), NC884 (2.5 µM), and NC2459 (312 nM) induce annexin binding in *L. major* promastigotes and not in murine intraperitoneal macrophages at concentrations that are toxic to parasites. (A-B) Percentages of parasites and macrophages emitting green fluorescence signal (annexin +) or red fluorescence signal (necrotic). (C) Representative flow cytometric dot plots used to quantify the percentages of green and red signal. IPM, BALB/c mice isolated intraperitoneal macrophages. *L. major* promastigotes and IPM treated were analyzed using Annexin-V/propidium iodide staining. C, negative control cells treated with 1% DMSO; C1, necrosis control parasites treated with 2 mM $H_2O_2$; C2, apoptosis control cells treated with 200 µM $H_2O_2$ in *L. major* and 2 mM $H_2O_2$ in macrophages.

It has been reported that some α,β-unsaturated ketones markedly increased the percentage of apoptotic cells in human pancreatic cancer cells through the depletion of intracellular thiols such as glutathione. Therefore, it is important to determine whether these compounds may have a similar effect on *L. major*. To assess the mode of cell death induced by candidate compounds, annexin-V/propidium iodide staining was performed. Externalization of phosphatidylserine (PS) seems to be the general feature of early stage apoptosis in most organisms, however, it has been recently reported that *L. major* promastigotes lack PS, nonetheless upon permeabilization or miltefosine treatment annexin V bind to the parasite membrane. Generally, PS is the major phospholipid detected in most apoptosis assays, however, not only PS is affected during this process as during apoptosis the asymmetric lipid arrangement in the plasma membrane is compromised, resulting in extreme changes in the phospholipid composition of both leaflets. It was found that despite lacking PS, annexin V is able to bind other phospholipid species such as PI and PE in *L. major* promastigotes likely as a consequence of changes in the plasma membrane lipid arrangement. Annexin V, which has strong $Ca^{2+}$-dependent affinity for PS, was used to measure the percentage of annexin positive *L. major* parasites and macrophages in response to treatment with compounds NC901, NC884, and NC2459. The annexin $V^-/PI^-$ population was regarded as normal cells, while positive staining just for annexin V was used as a measure of early changes in the lipid arrangement of the plasma membrane and annexin $V^-/PI^+$ was related to late changes in the lipid arrangement of the plasma membrane or necrosis. It was observed that all three compounds significantly induced an apoptosis-like effect in *L. major* promastigotes in comparison to the 1% DMSO treated controls (FIG. 8A). In order to determine whether these concentrations of drug that have shown to be toxic to the parasites are inducing apoptosis in mammalian cells, the same concentrations were tested in isolated intraperitoneal macrophages from BALB/c mice. No effect was observed in the macrophages treated with our three candidate compounds at the same concentrations that induced a significant percentage of annexin positive cells in *L. major* promastigotes (FIG. 8B).

Figure 9A:
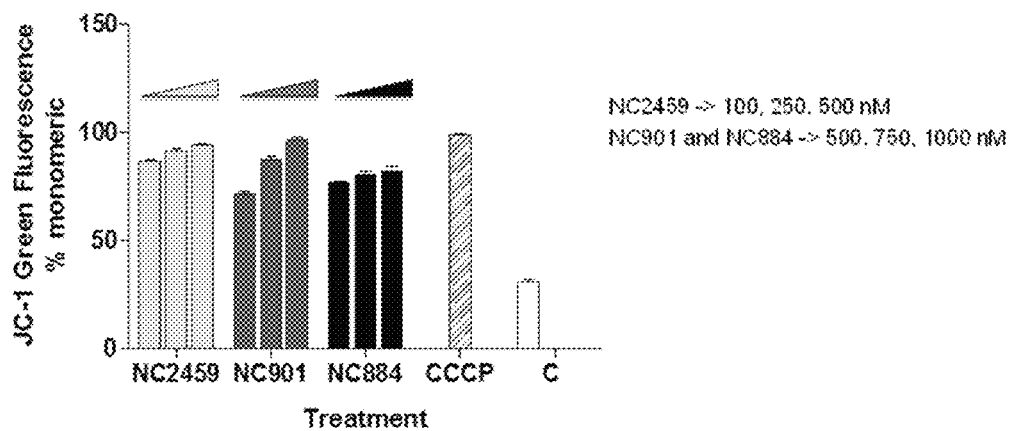
FIG. 9A-9B. Mitochondrial membrane depolarization of *L. major* promastigotes treated with the enone compounds NC884, NC901, and NC2459. The parasites were treated with several concentrations of the NC compounds and analyzed using the Mitoprobe™ JC-1 assay. C, negative control 1% DMSO; CCCP (50 µM), positive control. (A) Percentages of parasites emitting green fluorescence in response to treatment. (B) Representative flow cytometric dot plots used to quantify the percentages of green signal.
Figure 9B:
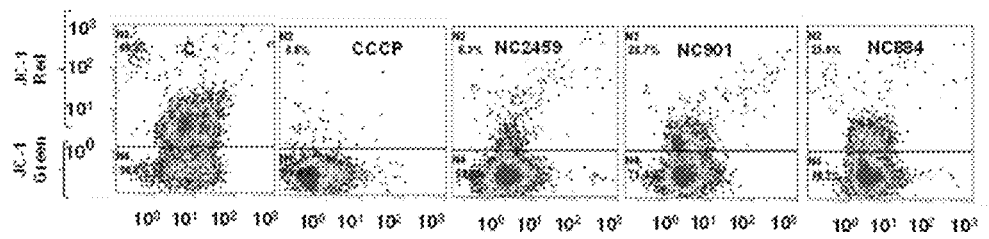

The disruption of the mitochondrial membrane potential ($\Delta_{\psi m}$) is a characteristic feature of apoptosis and other forms of cellular disfunction and death. Both in multicellular and unicellular organisms, the mitochondrion is an important cellular source for the generation of reactive oxygen species (ROS) inside cells, which serve as inducing signals for apoptosis. To determine the changes in the $\Delta_{\psi m}$ the Mitoprobe™ JC-1 assay was used. JC-1 exhibits potential dependent accumulation in mitochondria, indicated by a fluorescence emission shift from green (~529 nm) to red (~590 nm). A mitochondrial membrane potential disrupter known as CCCP (carbonyl cyanide 3-chlorophenylhydrazone) was used as our positive control. All three candidate compounds caused a concentration dependent loss in $\Delta_{\psi m}$ in comparison to the negative control treated with 1% DMSO (FIG. 9). Therefore, these results suggest that the apoptosis-like effect induced by compounds NC901, NC884, and NC2459 in *L. major* promastigotes is mitochondrial dependent.

B. Methods

Synthesis of α,β-Unsaturated Ketones and Preparation of NC Library.

The synthesis of NC901 and NC884 has been described previously. The preparation of NC2459 was achieved by the acylation of 3,5-bis(benzylidene)-4-piperidone with oxalyl chloride. The 136 compound library was shipped to the BBRC High-throughput Core Facility (HTSCF) from the University of Saskatchewan in Canada in powdered stocks. The powdered stocks were diluted in DMSO at varying concentrations depending on their solubility in DMSO. Each compound was added to one well in a 96-well plate to be used for drug screening.

Trypanosomatid Cultures.

Trypomastigote forms of *T. cruzi* Y strain were obtained from infected BALB/c mice by cardiac puncture four days following the intraperitoneal infection with $10^5$ parasites. The procedure was performed minimizing the distress and pain for the animals following the NIH guidance and animal protocol approved by UTEP's Institutional Animal Care and Use Committee (IACUC). Cell-derived trypomastigotes were initially obtained by infecting Green monkey kidney-derived LLC-MK2 cells (American Type Culture Collection-ATCC, Rockville, Md.). Briefly, semi-confluent host cell monolayers were maintained in DMEM medium (Invitrogen), supplemented with 10% heat-inactivated fetal bovine serum (DMEM-10% FBS), at 37 C, in 5% $CO_2$ humidified atmosphere. Cells were infected with trypomastigotes at 1:10 host cell/parasite ratio. Four days following the infection, trypomastigotes were harvested from the culture supernatant, centrifuged in 50-ml sterile, endotoxin-free conical polypropylene tubes (Fisher Scientific) (15 min, 3,000×g, 4 C), washed twice in 5 ml fresh DMEM-10% FBS, resuspended in the same medium, and used in the assays described below. To maintain the trypomastigote virulence, a maximum of nine in vitro passages (infections) were performed. The epimastigote forms of *T. cruzi* (Y strain) were grown in liver infusion-tryptose (LIT) medium. Mammalian cell-derived trypomastigote forms of *T. cruzi* (Y strain) were obtained from infected LLC-MK2 cells (American Type Culture Collection-ATCC, Manassas, Va.) monolayers as described. Promastigote forms of *L. major* strain Friedlin clone V1 were grown in RPMI 1640 medium (RPMI) supplemented with 30 mM hemin and 10% FBS inactivated and 50 ng/ml streptothricin neosulfate for maintenance of the LUC gene.

Culture of Mammalian Cells.

Rhesus monkey kidney epithelial cell LLC-MK2 (American Type Culture Collection-ATCC, Manassas, Va. # CCL-7), Hs-27 human fibroblasts (American Type Culture Collection-ATCC, Manassas, Va.), RAW 264.7 murine macrophages (American Type Culture Collection-ATCC, Manassas, Va.) U2-09 human osteoblasts (American Type Culture Collection-ATCC, Manassas, Va. # HTB-99) (American Type Culture Collection-ATCC, Manassas, Va.) cells were cultured in Dulbecco's Modified Eagle's Medium (DMEM), supplemented with 10% inactivated FBS, along with 1% of 10,000 units/ml penicillin and 10 mg/ml streptomycin in 0.9% sodium chloride. Intraperitoneal BALB/c mice macrophages were obtained and cultured in DMEM high-glucose, +L-glu, supplemented with 10% FBS (inactivated). The procedure was performed minimizing the distress and pain for the animals following the NIH guidance and animal protocol approved by UTEP's Institutional Animal Care and Use Committee (IACUC).

Evaluation of the NC library activity against *Leishmania major*. The NC library (136 compounds) was screened using firefly luciferase-expressing *L. major* promastigotes referred to as Lmj-FV1-LUC-TK (*L. major* strain Friedlin (MHOM/JL/80/Friedlin) clone V1) engineered to express luciferase following integration of the construct pIR1SAT-LUC(a)-TK (b) (strain B5113) in the rRNA locus (S. M. Hickerson and S. M. Beverley, unpublished data). Enones (stock solutions in DMSO) were diluted (1 nM to 500 µM, in a final 1% DMSO) and added (1 µl per well) to 96-well microplates using an Eppendorf epMotion 5070 automated pipetting system. Promastigotes ($10^6$/well) were added, and parasite survival was assessed by luciferase activity with the substrate 5'-fluoroluciferin (ONE-Glo Luciferase Assay System, Promega) after 96-h incubation at 28° C., using a luminometer (Luminoskan, Thermo). The bioluminescent intensity was a direct measure of the survival of parasites. This was determined by comparing bioluminescent intensity of *L. major* parasites live/dead with MTT assay and cell counting. The primary compound screens were performed as single wells. The "hit" (positive) were compounds with anti-parasitic activity (<25% inhibition of survival). Only drugs that were non-toxic or with low toxicity to mammalian cells were further investigated, and assayed in triplicate in three independent experiments, the half maximal effective concentrations ($EC_{50}$) were determined for each drug.

Viability assay on mammalian cells and *T. cruzi* epimastigotes. The cytotoxicity and anti-trypanosomal activity of the NC compounds was tested in human Hs27 fibroblasts (ATCC CRL-1634), LLC-MK$_2$ cells (ATCC CCL-7), RAW 264.7 murine macrophages (ATCC TIB71) (American Type Culture Collection-ATCC, Manassa, Va.), mice intraperitoneal macrophages and in epimastigote forms of *T. cruzi* Y strain using Alamar Blue assay (Invitrogen—Life Technology, Grand Island, N.Y.). The experiments were performed as described using a range of concentration of 500 µM to 1 nM.

In vitro evaluation of the NC drug library on infectivity experiments by high-content imaging assay. Mice intraperitoneal macrophages and human osteoblasts were placed in a microplate and infected with the amastigote forms of *L. major* strain Friedlin clone V1 and *T. cruzi* Y strain respectably, followed by treatment with NC lead compounds (as shown in Table 1). Briefly, Image acquisition and analyses of the plates were carried out using the BD Pathway 855 high-resolution fluorescence bioimager system (BD Biosciences). Filter sets appropriate for the excitation and emission spectra of Draq5 were utilized. Images from four fields (3×3 montage) were acquired per well with a 20× objective. To perform the host cell segmentation and counting of parasites, the BD AttoVision™ v1.6.2 Sub Object analysis was used. Draq5 creates a background, staining the host cell and parasite nucleus, but defining the cytoplasm as well, determining this way the amount of parasites within each mammalian cell. The host cell nucleus was excluded by size difference. Subsequently, the infection index was calculated based on the mean of these triplicate values by multiplying the percentage of infected cells and the constraints used in the HCIA assay that was of 2, 3, 5, and 8 parasites per cell.

Mice Strains.

Female BALB/c mice (6 to 8 week old) were purchased from Harlan Laboratories (Indianapolis, Ind.).

In Vivo Experiments.

The in vivo experiments were comprised of four groups of five mice each: (1) infected, but not treated [control for the infection—100 µL of DMSO per day, drug diluent]; (2) treated with NC884, NC901 or NC2459, but not infected with the parasites [control for drug toxicity]; (3) infected with the parasites and treated with amphotericin B (8 mg/kg/day) [reference drug; positive control]; and (4) infected with the parasites and treated with NC884, NC901 or NC2459 [experimental group]. Luciferase expressing metacyclic promastigotes *L. major* (Freidlin V1) were obtained as described previously. Suspensions of $1\times10^5$ or $1\times10^6$ parasites per 50 µl of sterile DMEM (endotoxin-free) were injected with a 30G needle into the left hind footpad of BALB/c mice. Two weeks post-infection the compounds were administered once a day by intraperitoneal route, daily for 14 to 17 days. Twice a week, weights were recorded to monitor toxicity and the thickness of the infected footpad and the non-infected footpad was measured with digital calipers to monitor the progression of the disease. The parasitic load also was evaluated through in vivo imaging using luminescence (Kodak Image Station). The mice were injected intra-peritoneally with 150 mg/kg D-luciferin (Sigma, USA) 10 min before imaging, anesthetized with 1-2% isofluorane in oxygen during imaging and the net intensity emitted from the footpad was quantified using the KODAK Image Station software. Parasite burden was expressed as net intensity emitted from *L. major* infected footpad lesions normalized against the background fluorescence of uninfected mice. The presence/absence of parasites was confirmed by PCR using *L. major* methionine aminopeptidase (MetAP1) 1 specific primers: 5'-GGATCCATGC-CCTGCGAAGGCTGCGGC-3' (SEQ ID NO:1) and 5'-GAATTCTCAGATTTTGATTTCGCTGGGGTCT-TCGG-3' (SEQ ID NO:2) on cDNA reverse transcribed from total RNA extracted from footpad lysate obtained by macerating footpad tissue fragments in Trizol (Invitrogen Life Technologies, United States) with the gentleMACS™ Dissociator (Miltenyi Biotec GmbH, Germany) following the manufacturer's protocol.

Detection of Apoptosis-Like Effect by Annexin V Assay.

Apoptosis was evaluated using Alexa Fluor® 488 Annexin V/PI Apoptosis Kit (Initrogen™-Life technology, Grand Island, N.Y.). *L. major* promastigotes and BALB/c mice intraperitoneal macrophages were treated with each compound for 24 h. After exposure, the parasites ($5\times10^7$) and macrophages ($5\times10^6$) were harvested, washed and re-suspended with PBS. The Annexin V/PI staining of cells followed the manufacturer's instructions. Then the samples were analyzed with Beckman Coulter Fc500 flow cytometer (Beckman Coulter, USA). The results were expressed as the number of annexin positive cells per thousand cells counted.

Polychromatic Analysis of Mitochondrial Membrane Potential ($\Delta_{\psi m}$).

*L. major* promastigotes and intraperitoneal macrophages from BALB/c mice were treated with each compound at three concentrations for four hours. Then, cells were stained with 2 µM of the fluorophore 5,5',6,6'-tetrachloro-1,1',3,3'-tetraethylbenzimidazolylcarboncyanine iodide (JC-1) following a modified version of manufacturer's instruction (Life Technologies, Grand Island, N.Y.). The disruption of mitochondrial $\Delta_{\psi m}$ is evidenced by an appreciable shift of the fluorescence signal from red to green. JC-1 aggregates or monomers, emitting red or green signal, were identified via flow cytometer (Cytomics Fc500) by using FL-2 or FL-1 detectors, respectively. A proton ionophore that dissipates the mitochondrial $\Delta_{\psi m}$ carbonyl cyanide 3-chlorophenylhydrazone (CCCP) at 50 µM, was used as a positive control. Cells treated with the diluent of the compounds (DMSO) and untreated were used as negative controls. Data collection and analysis was performed by using CXP software (Beckman Coulter). JC-1 is the most widely applied method for detecting mitochondrial depolarization occurring in the early stages of apoptosis.

Statistical Analysis.

The statistical significance (p-value) of the compound's cytotoxicity was calculated using the General Linear Mixed Model Analysis. This analysis was used to test the linear effect of the logarithm of dose on the logit transformation of the percent survival. The $IC_{50}$ was obtained as the exponent of the negative ratio of the y-intercept and the slope of the fitted regression line (SAS Software, Version 9.2). The graphs for display were attained using Graph Pad Prism 5 Software (GraphPad Software, Inc., La Jolla, Calif.). All experiments had statistical significance determined at $p \leq 0.05(*)$, $p \leq 0.01()$, and $p \leq 0.001(*)$.

The invention claimed is:

1. A method for treating a trypanosomatid infection in a subject, comprising administering to the subject a pharmaceutically effective amount of a compound having the chemical formula of:

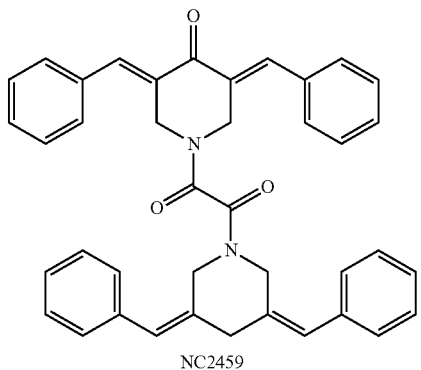

Formula 1

NC2459

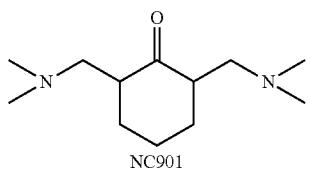

Formula II

NC901 or

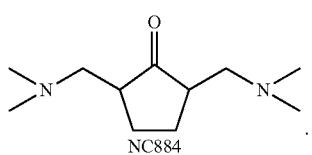

Formula III

NC884

2. The method of claim 1, wherein the trypanosomatid is a *Leishmania*.

3. The method of claim 2, wherein the trypanosomatid is *Leishmania major*.

4. The method of claim 1, wherein the trypanosomatid is a Trypanosome.

5. The method of claim 4, wherein the trypanosomatid is *Trypanosoma cruzi*.

6. The method of claim 1, further comprising administering a second anti-trypanosomatid therapy.

7. The method of claim 6, wherein the second anti-trypanosomatid therapy is an antibiotic or vaccine therapy.

* * * * *

UNITED STATES PATENT AND TRADEMARK OFFICE
CERTIFICATE OF CORRECTION

PATENT NO. : 9,669,016 B2
APPLICATION NO. : 15/193589
DATED : June 6, 2017
INVENTOR(S) : Rosa A. Maldonado et al.

Page 1 of 1

It is certified that error appears in the above-identified patent and that said Letters Patent is hereby corrected as shown below:

In the Specification

Please replace Column 1, Lines 14-16 with the following:
This invention was made with government support under GM008012 awarded by the National Institutes of Health. The government has certain rights in the invention.

Signed and Sealed this
Thirty-first Day of December, 2024

Derrick Brent
*Acting Director of the United States Patent and Trademark Office*